United States Patent [19]

Oda

[11] Patent Number: 5,126,938
[45] Date of Patent: Jun. 30, 1992

[54] COMPUTERIZED TOMOGRAPHY SYSTEM

[75] Inventor: Minoru Oda, Hyogo, Japan

[73] Assignee: Mitsubishi Denki Kabushiki Kaisha, Tokyo, Japan

[21] Appl. No.: 335,436

[22] Filed: Apr. 10, 1989

[30] Foreign Application Priority Data

Jul. 20, 1988 [JP] Japan ................. 63-179066

[51] Int. Cl.⁵ .......................... G06F 15/00
[52] U.S. Cl. ............................. 364/413.16
[58] Field of Search ................... 364/413.16

[56] References Cited

U.S. PATENT DOCUMENTS

| | | | |
|---|---|---|---|
| 4,010,371 | 3/1977 | LeMay | 364/413.16 |
| 4,135,247 | 6/1979 | Gordon et al. | 364/413.16 |
| 4,206,359 | 6/1980 | Hounsfield | 364/413.16 |
| 4,266,136 | 5/1981 | Duinker | 364/413.16 |
| 4,680,782 | 7/1987 | Tan et al. | 378/4 |

FOREIGN PATENT DOCUMENTS 8501531 12/1985 Netherlands .............. 378/4

OTHER PUBLICATIONS

Y. Iwai, Toshiba Medical Co., Ltd., "CT Scanner", 1979, pp. 139-141.

*Primary Examiner*—Dale M. Shaw
*Assistant Examiner*—Laura Brutman
*Attorney, Agent, or Firm*—Rothwell, Figg, Ernst & Kurz

[57] ABSTRACT

A computerized tomography system comprising a means for data rearrangement for converting fan-beam projection data into parallel beam projection data speedily andd easily without complicated calculations, said fan-beam projection data obtained at the detecting position corresponding to each defined pitch of rotary angle by which a detector unit comprising a number of radiation detectors arranged in a fan form against the radiation source is rotated.

13 Claims, 8 Drawing Sheets

COMPUTERIZED TOMOGRAPHY SYSTEM

BACKGROUND OF THE INVENTION

1. Field of the Invention

This invention relates to a computerized tomography (CT) system and more particularly, this invention relates to an improvement of an algorithm for reconstructing a tomogram.

2. Description of the Prior Art

FIG. 1 is a drawing of the constitution of a detector unit of a conventional CT system to perform the computerized tomography (CT). In the figure, 1 represents a radiation source such as X-ray source, $2_1$-$2_m$ represent radiation detectors such as X-ray detectors, 2 represents a radiation detector array composed by radiation detectors $2_1$-$2_m$, and 3 represents an imaging model. The radiation source 1 and the radiation detector array 2 collectively constituting a detector unit 4, the both being positioned to be interposed by the imaging model 3, are rotated and driven around the imaging model 3 with a driving unit not shown with the fixed relative positions to each other.

Operations are now explained. First, the radiation detectors $2_1$-$2_m$ detect radiation beams irradiated from the radiation source 1. The radiation beam emitted from the radiation source 1 transmits each part of the imaging model 3, to project to the radiation detectors $2_1$-$2_m$ at a radiation dose being attenuated by the absorption of the imaging model 3.

The radiation source 1 and the radiation detectors $2_1$-$2_m$ which constitute the detector units 4 mechanically integrated, gradually rotate around the imaging model 3 with the fixed relative positions to each other, interposing the imaging model 3 between them. Then, at each rotary position, the radiation source 1 projects radiation beams and then, detected signals of radiation which are detected by each radiation detector of $2_1$-$2_m$, are measured, respectively.

Thus, the function of this system is to determine the distribution image of the radiation absorption power of each part of the imaging model 3 which is calculated from detected signals on all rotary positions and to display it as a cross-sectional image on CRT. The detected data of the radiation detectors $2_1$-$2_m$ which transmit the imaging model 3 at a rotary position correspond to the fan-shaped distribution of the radiation beam and therefore, the converted data from the fan-beam projection data to parallel-beam projection data are required in order to calculate the distribution of radiation absorption power. Hence, as is conventional, data corresponding to parallel projection beam are calculated by interpolation from the fan-beam projection data and then, the distribution image of the radiation absorption power is reconstructed using an algorithm for image reconstruction such as filtered back projection method and the like.

Since the conventional computerized tomography system has been constituted in the way as described above, a large number of calculations for the interpolation have caused problems such as requirement of long time for the calculations. In addition, the calculations for interpolation have caused problems such that the spatial resolution of the absorption-power distribution image obtained as a result, gets deteriorated and the reconstructed image is of poor sharpness.

SUMMARY OF THE INVENTION

This invention has been performed to solve the above-mentioned problems and is designated to provide a computerized tomography system having a capability of reconstructing a tomogram at high speed without interpolating conversion calculations from fan-beam projection data to parallel-beam projection data.

The computerized tomography system according to the present invention, is provided with a means for data rearrangement which rearranges the data array of the fan-beam projection, obtained by a detector array arranged in a fan form against a radiation source.

DETAILED DESCRIPTION OF THE PREFERRED EMBODIMENTS

Figure 1:
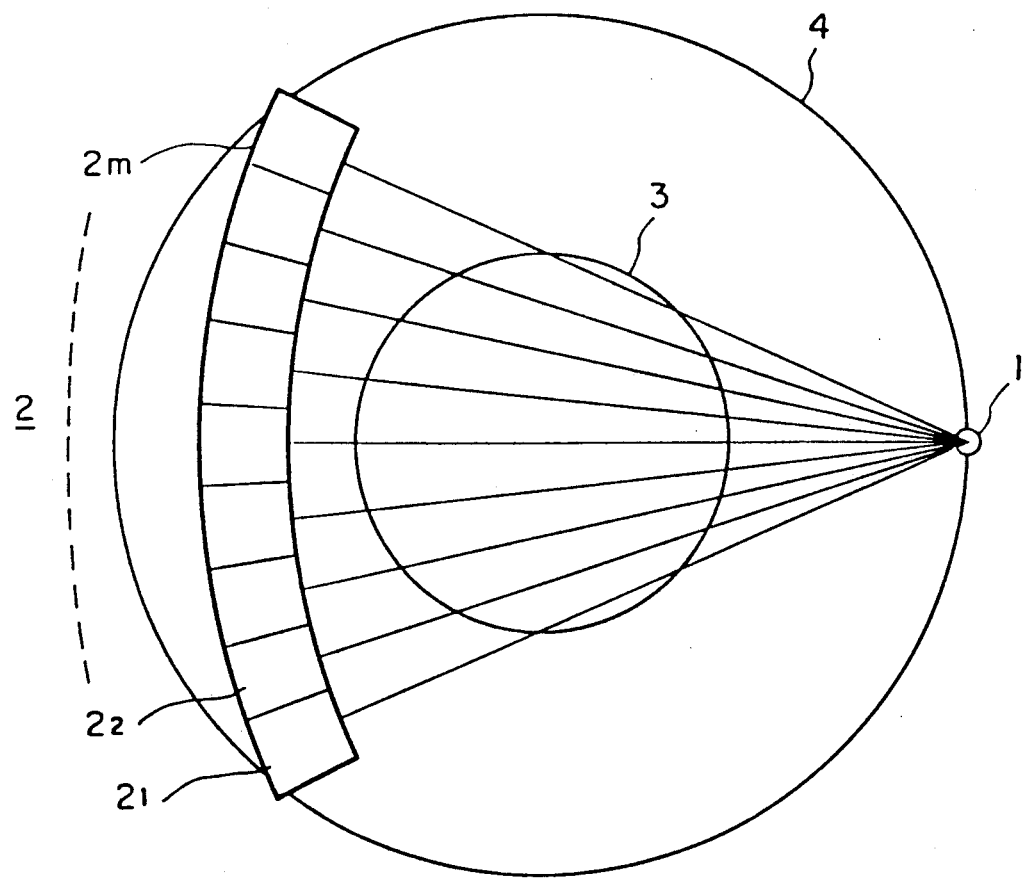
FIG. 1 is an arrangement drawing which shows the constitution of a conventional computerized tomography system.
Figure 2:
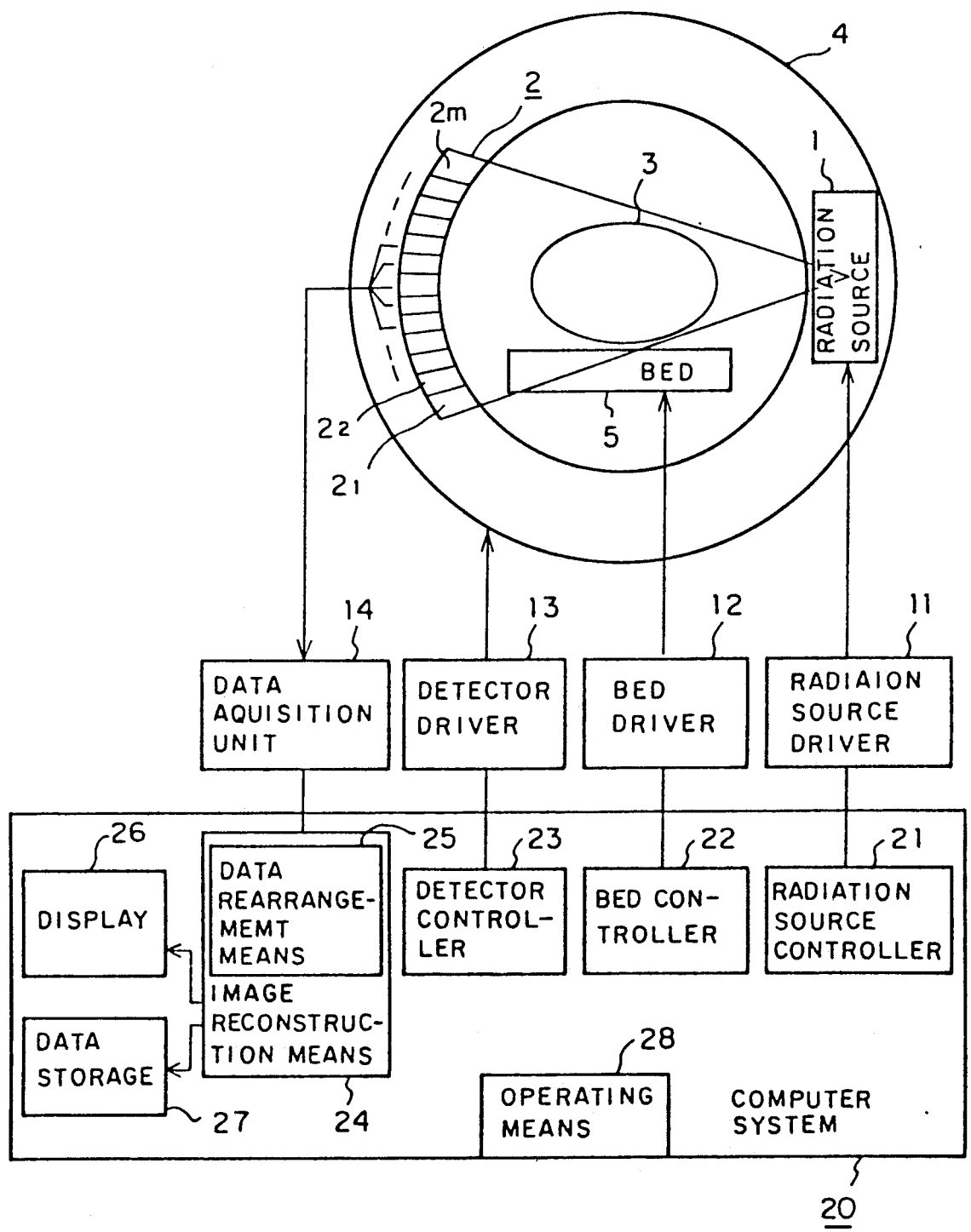
FIG. 2 is a block diagram which shows the constitution of a computerized tomography system according to the first embodiment in the present invention.

One of the embodiments in the present invention will be explained with reference to the drawings as follows. In FIG. 2 wherein the same parts are represented using the respective same symbols as those in FIG. 1, 5 represents a bed which can be moved in forward and backward directions in order to select imaging sections while supporting an imaging model (a patient or a subject for diagnosis); 11 represents a driving unit of X-ray tube so as to drive the radiation source 1; 12 represents a bed driving unit to move the bed 5 in order to determine the sectional position of the imaging model 3; 13 represents a driving unit of detectors which drive to rotate the detector unit 4 during the irradiations; 14 represents a signal registering part in which the output signals from each radiation detector of $2_1$-$2_m$ composing the radiation detector array 2 are collected and amplified to perform analog/digital conversion, followed by the transmittance to a computer system 20; 20 represents a computer system to control the total computerized tomography system and to reconstruct images: 21 represents a control means of X-ray tube, which controls the driving unit 11 of X-ray tube (a program segment); 22 represents a control means of bed which controls the bed driving unit 12; 23 represents a control means of the detectors to control the driving unit of detectors 13; 24 represents a means for image reconstruction for reconstructing a distribution image of X-ray absorption power of the imaging model 3 from parallel-beam data; 25 represents a means for rearrangement of data and conversion of data address; 26 represents a displaying unit of an image to produce the distribution image of X-ray absorption power; 27 represents a data memory unit for providing the storage of the image data or detected data; 28 represents an operational board (keyboard, etc.) to operate a computerized tomography system through the computer system 20. In addition, the radiation source 1 and the radiation detector array 2 are positioned on the same circle and each detector of $2_1$-$2_m$ is placed in an equal interval. The radiation source 1 and the radiation detector array 2 collectively composing the detector unit 4, is constituted in a fashion so that they can be driven and rotated around the imaging model 3 in the angle of 180° or 360° with the fixed relationship to their mutual positions.

Figure 3:
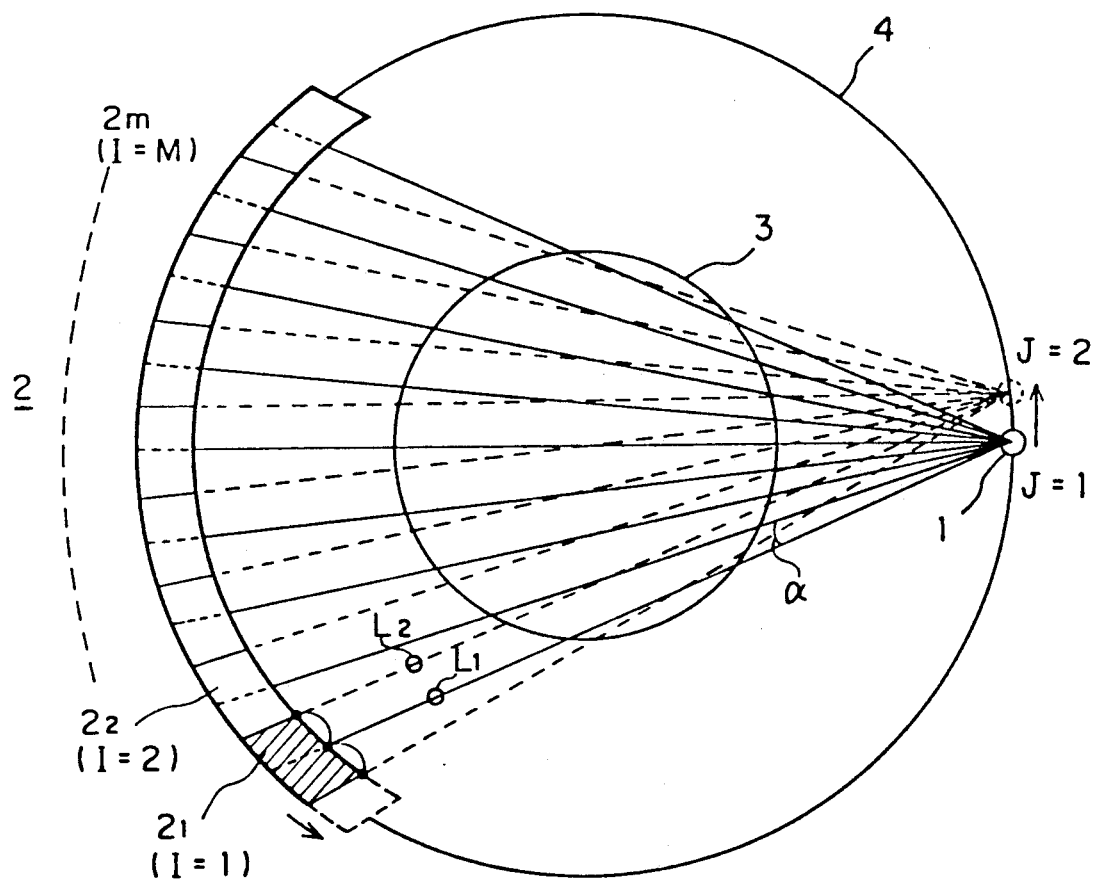
FIG. 3 is an arrangement drawing which shows the relative positions of the radiation source, the radiation detectors and the imaging model shown in FIG. 2.
Figure 4:
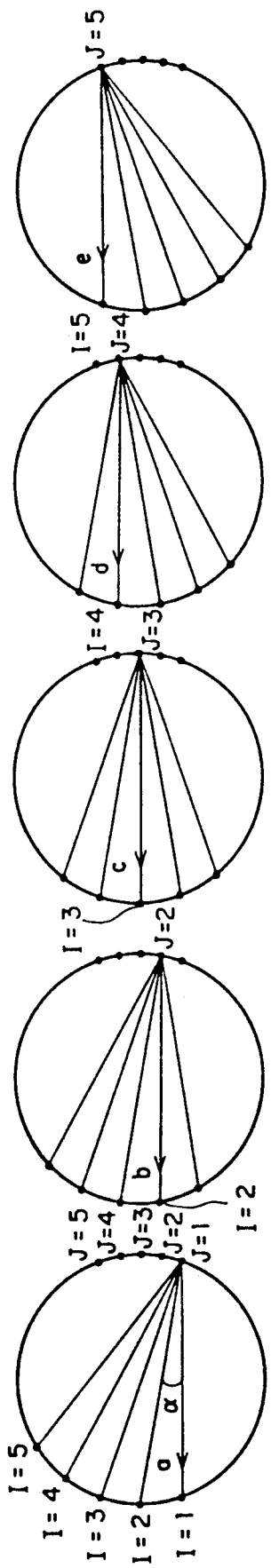
FIG. 4 is an explanatory drawing of a succession of irradiations in correspondence to stepwise rotational movements of the detector array and the radiation source.

As shown in FIG. 3, each of the radiation detectors is numbered as I from I=1 for the radiation detector $2_1$ to I=M for the detector $2_m$, and each of the angular coordinates at the irradiating positions of the radiation source 1 is defined as J.

Next, operations are explained referring the drawing in FIG. 3 showing the relationship of respective positions of each unit in accordance with the present invention. A first irradiation is performed while the detector unit 4 is placed at the position shown with solid lines (J=1) in the figure. A second irradiation is performed at the position shown with dotted lines (J=2) with the detector unit 4 rotated by an angle equal to the angle ($\alpha$) which the first detector $2_1$ and the second detector $2_2$ make to the radiation source 1. In this way, the radiation beam ($L_1$) incident to the first radiation detector $2_1$ before rotation, gets parallel to the radiation beam ($L_2$) incident to the second radiation detector 22 after rotation. As described above, the radiation source 1 and the radiation detectors $2_1$-$2_m$ are placed on the same circumference and with the equal interval between their positions and therefore, all angles which each radiation beam makes to adjacent each radiation detector are equal with $\alpha$. Accordingly, the above relationship between adjacent radiation beams corresponds to all radiation detectors and so, the radiation beam incident to the radiation detector (I) before rotation becomes parallel with the beam incident to the radiation detector (I+1) after rotation. At this time, the radiation detector array 2 progresses forward on the circumference by half of the distance between adjacent radiation detectors. In this way, the radiation detector array 2 repeats rotations by the equal, small angle step to result in the rotation of angle 180° or 360° while collecting data detected by each detector of $2_1$-$2_m$ at each rotary position; the data is expressed as D(I, J), where I is a detector number (1 to M), and J is a rotary angular coordinate (1 to N). Data D(I, J) which has the angular coordinates of J=I which is registered among data D(I, J), i.e. D(1, 1), D(2, 2), D(3, 3), etc. is regarded as the data obtained in the parallel radiation beam. Furthermore, data sets having the coordinate D(I, I+J) such as D(I, I+1), D(I, I+2), D(I, I+3), are also regarded as the data sets obtained by the parallel beam. FIGS. 4(a) to (e) show this relationship including that between the irradiation process and data registration. The figures consisting of Figs. (a), (b), (c), (d) and (e) sequentially represent the irradiation order for five times, for example (a) as a first irradiation and (b) as a second irradiation when the angle coordinate for imaging position is moved from J=1 to J=2. All the radiation beams of a, b, c, d and e illustrated in the figures described above are parallel to each other beam, as illustrated in Fig. (f). The data set of N pairs by parallel beam are obtained, after the data registration is performed over all the angle coordinates J (1 to N) in this way. In other words, if the data D(I, J) is rearranged to D(I, $J_0$), wherein $$J_0 = I + J \tag{1}$$

We get N sets of parallel beam data.

However, in the case of $J_0 = I + J > N$, the calculation by the following equation is performed in this process;

$$J_0 = I + J - N(I + J > N) \tag{2}$$

Figure 5:
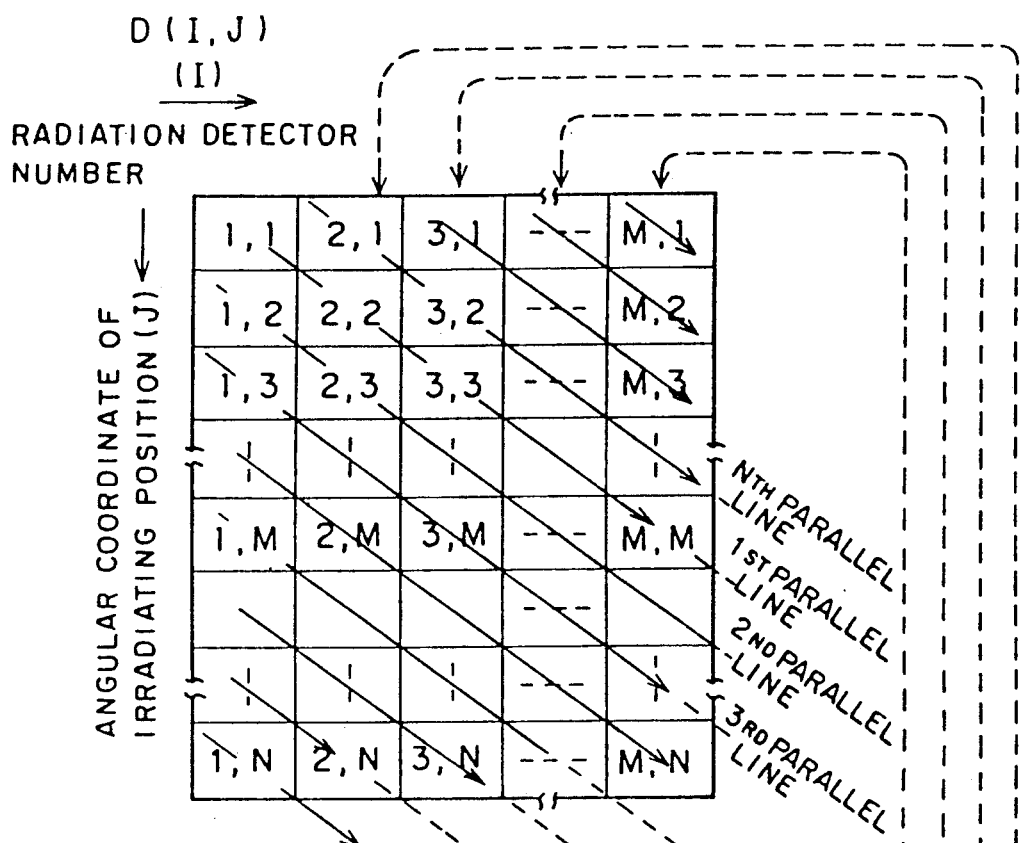
FIGS. 5(A) and (B) are arrangement drawings of data which show a relationship between data before and after processing in order to explain the method for data processing in the present invention.
Figure 5:
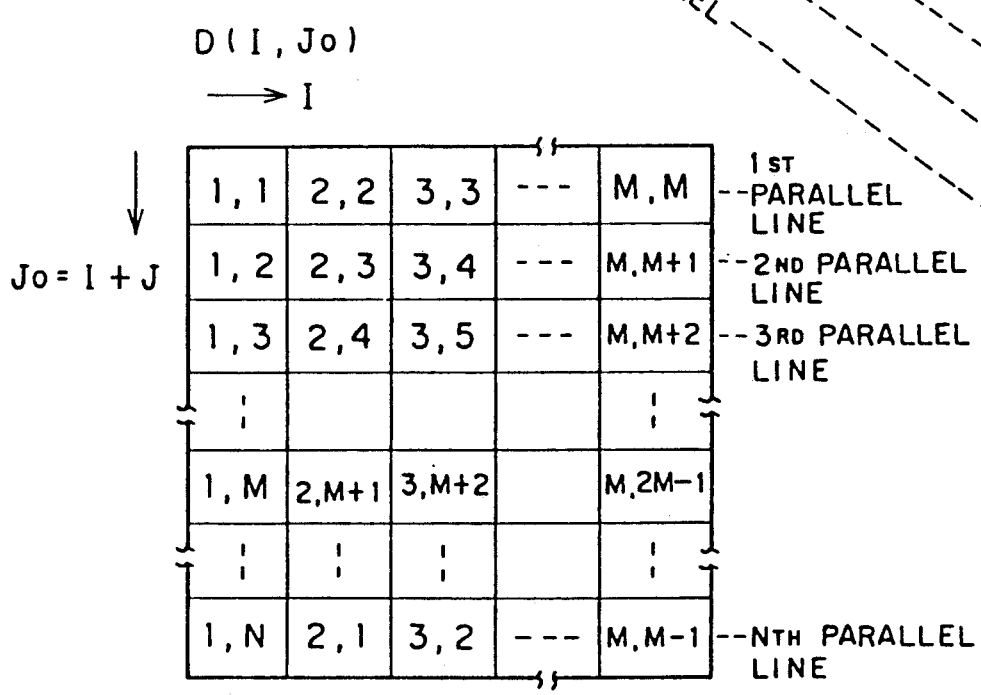

FIGS. 5(A) and (B) illustrate the rearrangement method of the above data, and (A) and (B), respectively, are the drawings before and after the data rearrangement. Thus, when both of the radiation source 1 and the radiation detector array 2 are rotated stepwise by the angle which is equal to the angle between the adjacent radiation beams to collect radiation data at each rotary position followed by the data rearrangement, the data by parallel beam can be immediately obtained, the radiation source 1 and the radiation detector array 2 being placed on the same circumference and the each detector of radiation detectors $2_1$-$2_m$ being positioned on the same circumference with the equal interval. Furthermore, the same result as above mentioned data rearrangement can be obtained by simply changing the order of read-out data from D(I, J) to D(I, $J_0$) as based on above mentioned address order [eqs. (1) and (2)]. FIG. 5(A) illustrates the order of data read-out as shown with arrowed lines. Accordingly, the conversion calculation by interpolation from data in fan-beam to those in parallel beam which is required in the conventional art is no more necessary to result in the decrease of the calculation procedure. Furthermore, the deterioration of the spatial resolution in the reconstructed image caused by interpolation can be avoided to lead to the quality improvement of the reconstructed image.

However, in accordance with this method, the data in parallel beam obtained by the rearrangement of the above data do not have strictly equal interval on the imaging model 3; that is, the interval gets narrower in the exterior part of the imaging model 3 than that in the center thereof. This causes an "X" shaped distortion to a reconstructed image but it's degree is quite slight, which is, for example, about 1% in the case where the divergent angle of fan-beam is assumed 30°; therefore, it may be practically allowed.

Figure 6:
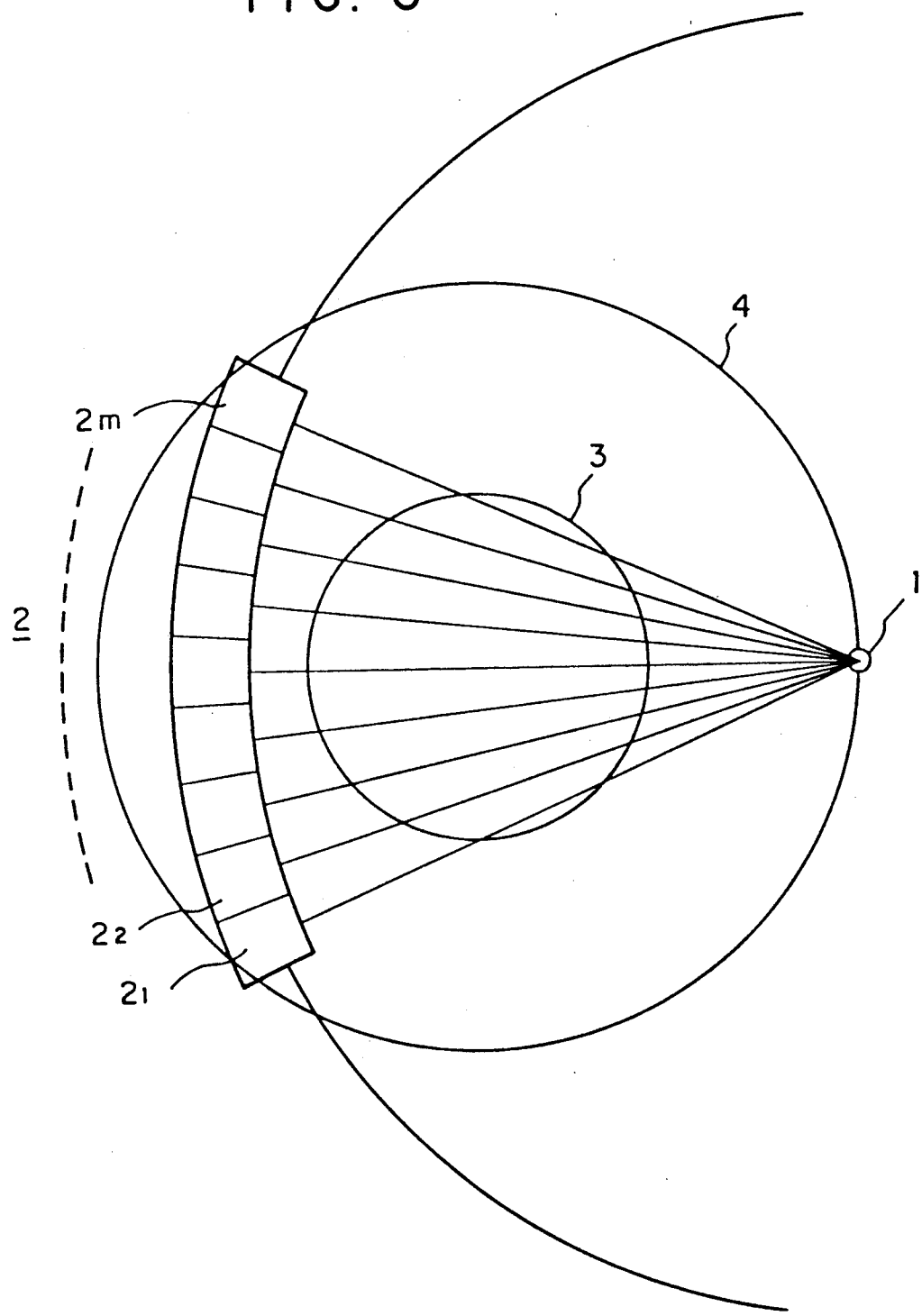
FIG. 6 is an arrangement drawing which shows the relative positions of the radiation source, the radiation detectors, and the imaging model in the computerized tomography system according to the second embodiment in the present invention.

FIG. 6 shows the second embodiment in accordance with the present invention. In the figure, the same symbols are used in the same or corresponding parts as those in FIG. 3. In FIG. 3, the radiation detectors $2_1$-$2_m$ are positioned on the same circumference as the radiation source 1 and with the equal interval; in FIG. 6, the radiation detectors $2_1$-$2_m$ are placed on the circumference of the circle having the radiation source 1 as its center and with an equal interval in order to arrange all adjacent radiation detectors to the radiation source in the equal angle. The position defined in FIG. 2 is one of means to set the equal angle between each fan-beam and the data collection and rearrangement to parallel beam data is also possible even in the arrangement shown in FIG. 6. Because all radiation detectors $2_1$-$2_m$ are placed against the radiation source 1 under the same condition in FIG. 6, it is easy to make a radiation detector with uniform properties; as a result, the radiation data demonstrate an excellent uniformity therein to result in the improvement of the quality of reconstructed image as a merit.

Figure 7:
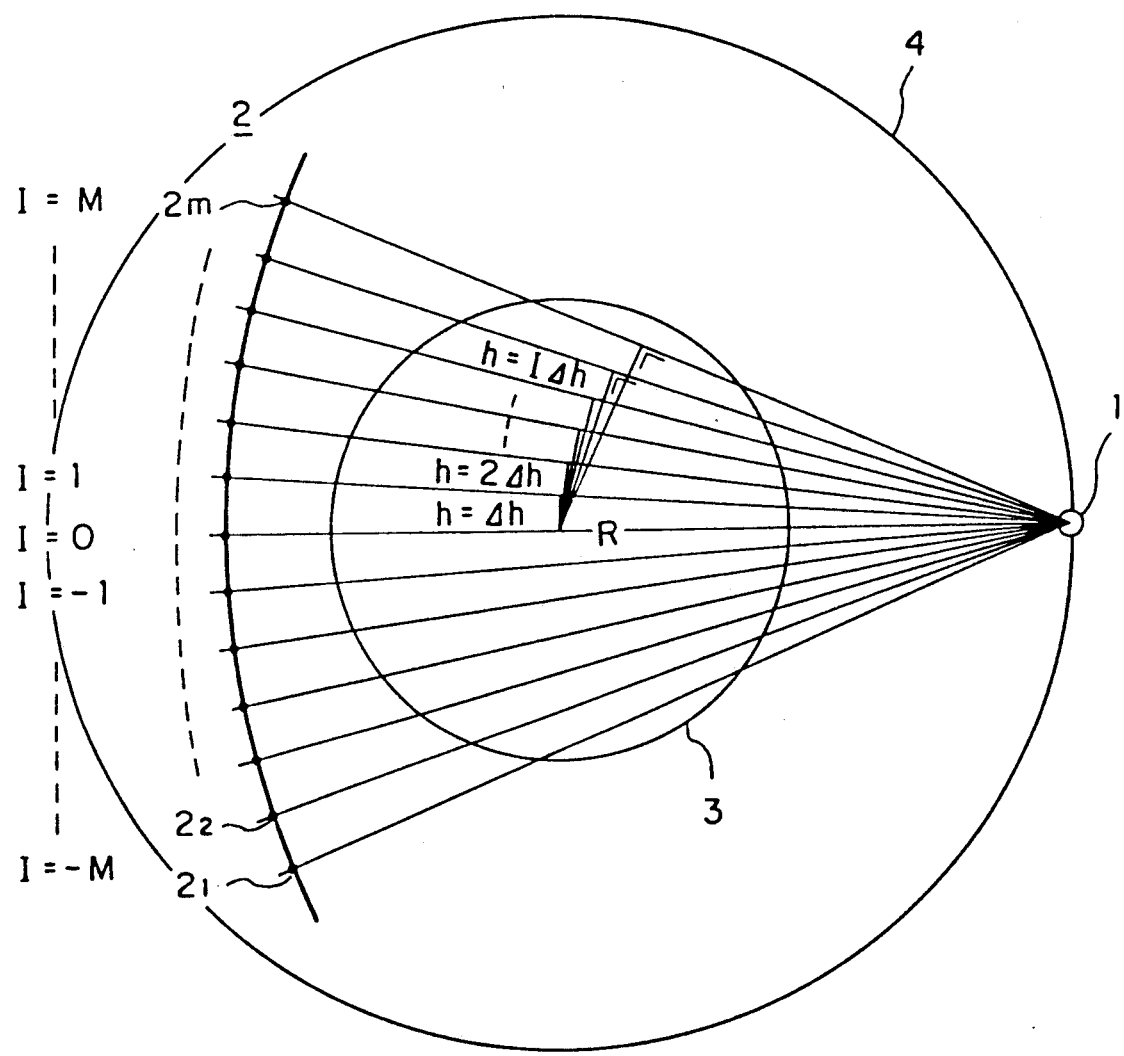
FIG. 7 is an arrangement drawing which shows the relative positions of the radiation source, the radiation detectors, and the imaging model in the computerized tomography system according to the third embodiment in the present invention.

FIG. 7 shows the third embodiment according to the present invention. In the figure, the same symbols are used in the same or corresponding parts as those in FIG. 3 and FIG. 6. The embodiments shown in FIG. 3 and FIG. 6 demonstrate slightly distorted reconstructed images as explained previously. More strictly, the same cause as those causing the distortion produces slightly diffused reconstructed image in the marginal region thereof. The above described defect in those embodiments in FIG. 3 and FIG. 6 is improved in the embodiments of FIG. 7. FIG. 7 shows how to place the radiation detectors $2_1$-$2_m$ In FIG. 7, the perpendicular line h which is drawn from the rotary center of the detector units 4 to the respective beam corresponding the radiation detectors $2_1$-$2_m$, is to have an equal increment $\Delta h$.

The above relationship can be expressed by the following equation;

$$\theta(I) = \sin^{-1}\left(\frac{I\Delta h}{R}\right) \approx \frac{I\Delta h}{R} - \frac{1}{6}\left(\frac{I\Delta h}{R}\right)^3 \quad (3)$$

where the detector in the center of the detector array 2 is numbered as I=0, then each the detector number is defined as I from $I = -M$ for the detector $2_1$ to I=M for the detector $2_m$ respectively; R is the distance between the radiation source 1 and the rotary center of the detector unit 4: $\theta(I)$ is the angle which the radiation beam incident to the radiation detector I makes to the center axis. In this case, angles between adjacent radiation beams are not equal, but getting larger as I is increasing.

Herein, the rotary pitch in angle is to be set equal to the angle which the radiation detector (I=0) in the center of the radiation detectors $2_1$-$2_m$ and the radiation detector adjacent thereto make to the radiation source 1. The data rearranged by the equation (1) and (2) may not be the corresponding data obtained in parallel beam in a strict meaning under the arrangement of the radiation detectors $2_1$-$2_m$ in the above described way. But the arrangement with an equal interval can be achieved on the imaging model 3. Accordingly, there is no distortion in the reconstituted images and the remarkable decrease in the image diffusion can be achieved. The ratio E of the image diffusion to the radius of image can be expressed in the following equation;

$$E = \frac{\theta^3}{6}\sqrt{1 - \frac{\sin^2\theta}{\sin^2\theta_{max}}} \quad (4)$$

wherein $\theta_{MAX}$ is the half angle of the radiation beam incident to the radiation detector in the most exterior edge.

In the case where the angle of fan beam is 30° ($\theta_{MAX}=15$), the maximum value of E is approximately 0.001 and therefore, it may be practically negligible.

Figure 8:
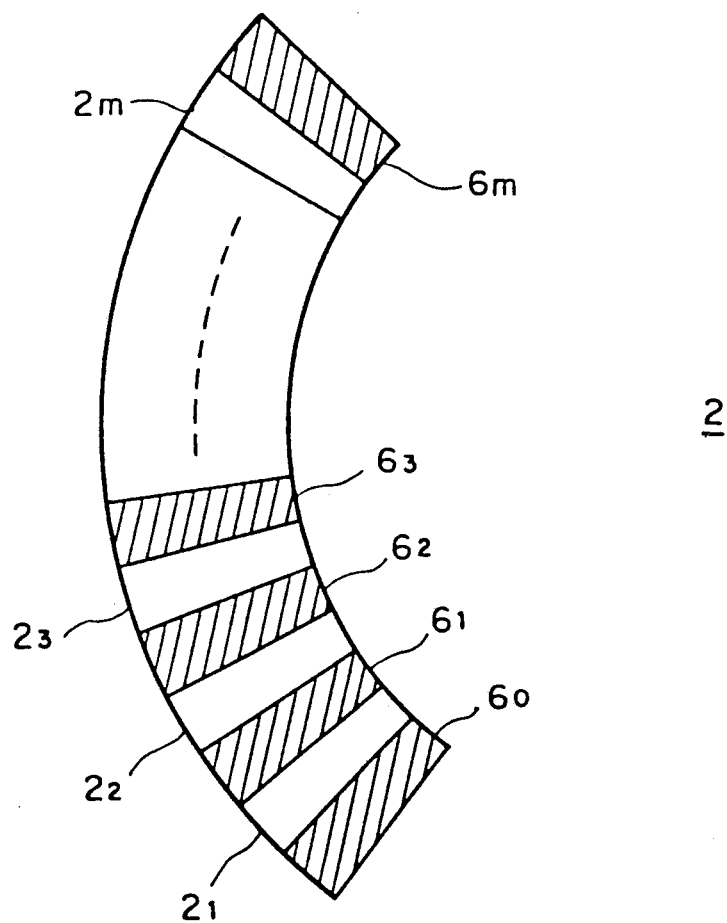
FIG. 8 is a construction drawing of a radiation detector array in the computerized tomography system according to the fourth embodiment in the present invention.

FIG. 8 shows the construction of a radiation detector array 2 employed in a computerized tomography system in a fourth embodiment according to the present invention. The radiation detector array 2 shown in FIG. 8 is applicable also to the computerized tomography systems in the first, second and third embodiments. The radiation detector array 2 comprises, in an alternate arrangement, radiation detectors $2_1, 2_2, 2_3, \ldots$, and $2_m$, and radiation shields $6_0, 6_1, 6_2, 6_3, \ldots$, and $6_m$ having a thickness the same as that of the radiation detectors.

As mentioned above, in the first embodiment (FIGS. 2 and 3), the angular pitch of rotation of the detector unit 4 is the same as the angle $\alpha$ formed between the adjacent radiation beams, and hence the radiation detectors $2_1, 2_2, 2_3, \ldots$, and $2_m$ are moved at a interval equal to half the pitch between the adjacent radiation detectors. It is known from this fact that a reconstructed image can be formed in an optimum spatial resolution when the circumferential thickness of the radiation detectors is equal to half the interval thereof. Suppose simply that only the spatial resolution matters. Then, it is desirable to form the radiation detectors in a minimum possible thickness. However, since the quantity of information of radiation decreases with the reduction of the thickness of the radiation detectors, an optimum thickness of the radiation detectors is half the interval of the radiation detectors in view of both the spatial resolution and the quantity of information. When the radiation detector array is constructed so as to meet the foregoing needs, gaps of a size equal to the radiation detectors thickness are formed respectively between the adjacent radiation detectors, and radiation shields can be provided respectively in the gaps.

The radiation shields disposed respectively in the gaps eliminate scattering radiation beams which deteriorate the contrast of the reconstructed image, to improve the contrast of the reproduced image remarkably. In the conventional computerized tomography system, priority is given to acquisition of a larger quantity, of radiation and efforts have been made to arrange the radiation detectors with smaller gaps therebetween, and hence it has been impossible to provide the conventional radiation detector array with such radiation shields. Although the apparent quantity of detectable radiation is reduced when the radiation detectors are arranged with gaps therebetween, improvement in both the spatial resolution and the contrast is equivalent to the substantial increase in the quantity of radiation, and the total effect of such improvement substantially increases the quantity of information of radiation.

In the second and third embodiments (FIGS. 6 and 7), the pitch of movement of the radiation detectors in operation for taking a tomogram is not, in a strict sense, half the interval of the radiation detectors, but the pitch of movement is approximately half the interval of the radiation detectors. Accordingly, a radiation detector array of a construction similar to that of the radiation detector array employed in the fourth embodiment is applicable to the second and third embodiments for the same improvement.

What is claimed is:

1. A computerized tomography system, wherein a radiation source projecting radiation beams and a radiation detector array for detecting the radiation beams from said radiation source integrally compose a detector unit which rotates around an imaging model and the radiation beam transmitted through the imaging model, while the detector units rotates, is detected with each radiation detector of the radiation detector array, and the obtained imaging data is calculated and processed with a computer system to get a tomogram of said imaging model, said computerized tomography system being characterized by;

each of the radiation detectors being arranged so that the vertical line which is drawn from the rotary center of said detector unit to said radiation beam corresponding to the respective radiation detector has an equal increment, and comprising;

a driving means for the detector unit to rotate and move the detector array to a plurality of predetermined detecting positions with the rotary angle pitch equal to an angle which a radiation detector at the center of the radiation detector array and a radiation detector adjacent thereto make to the radiation source, and a means of data rearrangement for rearranging the image data of the individual radiation detectors and of the individual detecting positions.

2. A computerized tomography system according to claim 1, wherein said means for data rearrangement is realized by said computer system.

3. A computerized tomography system, wherein a radiation source emitting radiation beams and a radiation detector array for detecting the radiation beams from said radiation source integrally compose a detector which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by; each of the radiation detectors and the radiation source being arranged so that the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above;

a means for data rearrangement to rearrange the image data of the individual radiation detectors and of the individual detecting positions;

said radiation source and said radiation detector array being arranged on a circumference with the center thereof being a rotary center of said detector unit, wherein said means for data rearrangement is realized by the computer system;

said computer system comprises a means for accumulating image data in a data memory unit in the form of a column and row matrix D(I, J), where I is a detector number (1 to M)and J is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

4. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged sot hat the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above, and a means for data rearrangement to rearrange the image data of the individual radiation detectors and of the individual detecting positions;

said radiation detector array is arranged on a circumference with the center thereof being positioned by said radiation source;

said means for data rearrangement is realized by the computer system;

said computer system comprises a means for accumulating image data in a data memory unit in the form of a column and row matrix D(I, J), where I is a detector number (1 to M) and J is a rotary angular coordinate (1 to N), and means for data read-out in a rearranged column and row matrix $(D_1(I, J_0)$, where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

5. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged so that the radiation source makes an angle to each of the radiation detectors of the radiation detector array, said angle being equal to the angle which the radiation source makes tot he detector adjacent thereto, and comprising:

a driving means for the detector unit to rotate and move the detector unit to a plurality of predetermined detecting positions with a rotary angle pitch equal to the angle described above, and a means for data rearrangement to rearrange the image data of the individual radiation detectors and of the individual detecting positions;

said radiation source and said radiation detector array being arranged on a circumference with the center thereof being a rotary center of said detector unit;

said means for data rearrangement is realized by the computer system;

said computer system comprises a means for accumulating image data in the data memory unit in the form of a column and row matrix $D(I, J)$, where $I$ is a detector number (1 to M) and $J$ is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

6. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged so that the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above, and a means for data rearrangement to rearrange the image data of the individual radiation detectors and of the individual detecting positions;

said radiation detector array is arranged on a circumference with the center thereof being positioned by said radiation source;

said means for data rearrangement is realized by the computer system;

said computer system comprises a means for accumulating image data in the data memory unit in the form of a column and row matrix $D(I, J)$, where $I$ is a detector number (1 to M) and $J$ is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

7. A computerized tomography system, wherein a radiation source projecting radiation beams and a radiation detector array for detecting the radiation beams from said radiation source integrally compose a detector unit which rotates an imaging model and the radiation beam transmitted through the imaging model, while the detector units rotate, is detected with each radiation detector of the radiation detector array, and the obtained imaging data is calculated and processed with a computer system to get a tomogram of said imaging model, said computerized tomography system being characterized by;

each of the radiation detectors being arranged so that the vertical line which is drawn from the rotary center of said detector unit to said radiation beam corresponding to the respective radiation detector has an equal increment, and comprising:

a driving means for the detector unit to rotate and move the detector array to a plurality of predetermined detecting positions with the rotary angle pitch equal to an angle which a radiation detector at the center of the radiation array and a radiation detector adjacent thereto make to the radiation source, a means of data rearrangement for rearranging the image data of the individual radiation detectors and of the individual detecting positions;

said means for data rearrangement is realized by said computer system;

said computer system comprises a means for accumulating image data in a data memory unit in the form of a column and row matrix $D(I, J)$, where $I$ is a detector number (1 to M) and $J$ is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

8. A computerized tomography system, wherein a radiation source projecting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained imaging data is calculated and processed with a computer system to get a tomogram of said imaging model, said computerized tomography system being characterized by;

each of the radiation detectors being arranged so that the vertical line which is drawn from the rotary center of said detector unit to said radiation beam corresponding to the respective radiation detector has an equal increment, and comprising:

a driving means for the detector unit to rotate and move the detector array to a plurality of predetermined detecting positions with the rotary angle pitch equal to an angle which a radiation detector at the center of the radiation detector array and a radiation detector adjacent thereto make to the radiation source, and a means of data rearrangement of rearranging the image data of the individual radiation detectors and of the individual detecting positions;

said means for data rearrangement is realized by said computer system;

said computer system comprises a means for accumulating image data in a data memory unit in the form of a column and row matrix $D(I, J)$, where I is a detector number (1 to M) and J is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction.

9. A computerized tomography system according to any one of claim 1, 2, 3, 4, 5, 6, 7 or 8, wherein the thickness of the radiation detectors of the radiation detector array is approximately half the interval of the radiation detectors, and radiation shields are disposed respectively between the adjacent radiation detectors and at both ends of the radiation detector array.

10. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged so that the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above;

a means for data rearrangement to rearrange the image data of the individual radiation detectors and of the individual detecting positions;

said radiation source and said radiation detector array being arranged on a circumference with the center thereof being a rotary center of said detector unit;

said means for data rearrangement is realized by the computer system;

said computer system comprises a means for accumulating image data in a data memory unit in the form of a column and row matrix $D(I, J)$, where I is a detector number (1 to M) and J is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction;

the thickness of the radiation detectors of the radiation detector array is approximately half the interval of the radiation detectors, and radiation shields are disposed respectively between the adjacent radiation detectors and at both ends of the radiation detector array.

11. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged so that the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above;

a means for data rearrangement to rearrange the image data of the individual radiation detectors and of the individual detecting positions;

said radiation detector array is arranged on a circumference with the center thereof being positioned by said radiation source;

said means for data rearrangement is realized by the computer system;

said computer system comprises a means for accumulating image data in a data memory unit in the form of a column and row matrix $D(I, J)$, where I is a detector number (1 to M) and J is a rotary angular coordinate (1 to N), and means for data read-out in a rearranged column and row matrix $D_1(I, J_0)$, where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction;

the thickness of the radiation detectors of the radiation detector array is approximately half the interval of the radiation detectors, and radiation shields are disposed respectively between the adjacent radiation detectors and at both ends of the radiation detector array.

12. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source so that the radiation source being arranged makes and angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above;

a means for data rearrangement to rearrange the image data of the individual radiation detectors and of the individual detecting positions;

said radiation source and said radiation detector array being arranged on a circumference with the center thereof being a rotary center of said detector unit;

wherein said means for data rearrangement is realized by the computer system;

said computer system comprises a means for accumulating image data in the data memory unit in the form of a column and row matrix D(I, J), where I is a detector number (1 to M) and J is a rotary angular coordinate (1 to N), and means for data read-out in a rearranged column and row matrix $D_1$ (I, $J_0$), where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction;

the thickness of the radiation detectors of the radiation detector array is approximately half the interval of the radiation detectors, and radiation shields are disposed respectively between the adjacent radiation detectors and at both ends of the radiation detector array.

13. A computerized tomography system, wherein a radiation source emitting radiation beams and a radiation detector array for detecting the radiation beams from said radiation source integrally compose a detector unit which rotates around an imaging model and the radiation beam transmitted through the imaging model, while the detector units rotate, is detected with each radiation detector of the radiation detector array, and the obtained image data is calculated and processed with a computer system to get a tomogram of said imaging model, said computerized tomography system being characterized by;

each of the radiation detectors and the radiation source being arranged sot hat the radiation source makes an angle to each of the radiation detectors of the radiation detector array, said angle being equal to the angle which the radiation source makes to the detector adjacent thereto, and comprising:

a driving means for the detector unit to rotate and move the detector unit to a plurality of predetermined detecting positions with a rotary angle pitch equal to the angle described above;

a means for data rearrangement to rearrange the image data of the individual radiation detectors and of the individual detecting positions;

said radiation detector array is arranged on a circumference with the center thereof being positioned by said radiation source;

said means for data rearrangement is realized by the computer system;

said computer system comprises a means for accumulating image data in the data memory unit in the form of a column and row matrix D(I, J), where I is a detector number (1 to M) and J is a rotary angular coordinate (1 to N), and means for data read-out in a rearranged column and row matrix $D_1$ (I, $J_0$), where $J_0$ is based on the address calculation as follows:

in the case of $I+J \leq N$, then $J_0 = I+J$, and
in the case of $I+J > N$, then $J_0 = I+J-N$ where each radiation detector of the radiation detector array is numbered respectively as I from 1 to I in clockwise direction and each angular coordinate of the irradiating positions is numbered respectively as J from 1 to N in counterclockwise direction;

the thickness of the radiation detectors of the radiation detector array is approximately half the interval of the radiation detectors, and radiation shields are disposed respectively between the adjacent radiation detectors and at both ends of the radiation detector array.

* * * * *

UNITED STATES PATENT AND TRADEMARK OFFICE
CERTIFICATE OF CORRECTION

PATENT NO. : 5,126,938

DATED : June 30, 1992

INVENTOR(S) : Minoru Oda

It is certified that error appears in the above-identified patent and that said Letters Patent is hereby corrected as shown below:

Title page, item [54] and col. 1, in the title, should read
--COMPUTERIZED TOMOGRAPHY SYSTEM WITH MEANS FOR RECONSTRUCTING IMAGE DATA FOR PARALLEL-BEAM PROJECTION DATA READ-OUT--.

Item [57] Abstract, line 4, "andd" should read --and--

Column 3, line 43, "22" should be --$2_2$--.

Column 5, line 34, in equation (3), the symbol before $\frac{1}{6}$ should be --+--.

Column 6, line 42, after "quantity" delete the comma ",".

Column 7, line 39, after "by;" begin a new paragraph.

Column 8, line 18, "sot hat" should be --so that--;
line 67, "tot" should be --to--;
line 68, "he" should be --the--.

Column 13, line 18, "and" should be --an--.

Column 14, line 16, "sot hat" should be --so that--.

Signed and Sealed this

Fourteenth Day of September, 1993

*Attest:*

BRUCE LEHMAN

*Attesting Officer*  *Commissioner of Patents and Trademarks*